United States Patent [19]

Boller et al.

[11] 4,198,130
[45] Apr. 15, 1980

[54] LIQUID CRYSTAL MIXTURES

[75] Inventors: Arthur Boller, Binningen; Alfred Germann, Munchenstein; Martin Schadt, Seltisberg; Hanspeter Scherrer, Therwill, all of Switzerland

[73] Assignee: Hoffmann-La Roche Inc., Nutley, N.J.

[21] Appl. No.: 907,961

[22] Filed: May 22, 1978

[30] Foreign Application Priority Data

Jun. 3, 1977 [CH] Switzerland .................. 6863/77
Apr. 11, 1978 [CH] Switzerland .................. 3868/78

[51] Int. Cl.² .................. C09K 3/34; C02F 1/13
[52] U.S. Cl. .................. 350/350; 252/299; 252/408
[58] Field of Search .................. 252/299, 408; 350/350

[56] References Cited

U.S. PATENT DOCUMENTS

| | | | |
|---|---|---|---|
| 4,000,084 | 12/1976 | Hsieh et al. | 252/299 |
| 4,029,595 | 6/1977 | Ross et al. | 252/299 |
| 4,062,798 | 12/1977 | Boller et al. | 252/299 |
| 4,076,646 | 2/1978 | Nakano et al. | 252/299 |
| 4,118,335 | 10/1978 | Krause et al. | 252/299 |
| 4,130,502 | 12/1978 | Eidenschink et al. | 252/299 |
| 4,154,697 | 5/1979 | Eidenschink et al. | 252/299 |

FOREIGN PATENT DOCUMENTS

| | | |
|---|---|---|
| 2257588 | 6/1973 | Fed. Rep. of Germany ........... 252/299 |
| 2348193 | 4/1974 | Fed. Rep. of Germany ........... 252/299 |
| 2548360 | 5/1977 | Fed. Rep. of Germany ........... 252/299 |
| 2557267 | 6/1977 | Fed. Rep. of Germany ........... 252/299 |
| 2708276 | 9/1977 | Fed. Rep. of Germany ........... 252/299 |
| 105701 | 5/1974 | German Democratic Rep. ..... 252/299 |

OTHER PUBLICATIONS

Eidenschink, R., et al., Angewanote Chemie, vol. 89, No. 2, p. 103 (1977).
Dewar, M. J., et al., J. Am. Chem. Soc., vol. 92, No. 6, pp. 1582–1586 (1970).

Primary Examiner—Leland A. Sebastian
Assistant Examiner—T. S. Gron
Attorney, Agent, or Firm—Jon S. Saxe; George M. Gould; William G. Isgro

[57] ABSTRACT

Liquid crystal mixtures having positive anisotropy of the dielectric constants comprising a nematogenic material having a clearing point above 60° C., one or more compounds of the formula

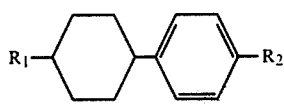

wherein $R_1$ and $R_2$ are hydrogen or straight-chain alkyl, provided that at least one of $R_1$ and $R_2$ is other than hydrogen and that $R_1$ and $R_2$ together contain no more than 9 carbon atoms, and, if desired, one or more additional doping agents, are described.

15 Claims, No Drawings

LIQUID CRYSTAL MIXTURES

BRIEF SUMMARY OF THE INVENTION

The invention relates to liquid crystal mixtures having positive anisotropy of the dielectric constants which comprises a nematogenic material having a clearing point above 60° C., one or more compounds of the formula

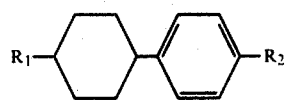

wherein $R_1$ and $R_2$ are hydrogen or straight-chain alkyl, provided that at least one of $R_1$ and $R_2$ is other than hydrogen and that $R_1$ and $R_2$ together contain no more than 9 carbon atoms,
and, if desired, one or more additional doping agents.

In another aspect, the invention relates to an electro-optical apparatus containing the liquid crystal mixtures set forth above.

In yet another aspect, the invention relates to a rotation cell containing the liquid crystal mixtures set forth above.

DETAILED DESCRIPTION OF THE INVENTION

The invention relates to liquid crystal mixtures having positive anisotropy of the dielectric constants, said mixtures contain or comprise a nematogenic material having a clearing point above 60° C., one or more compounds of the formula

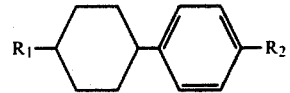

wherein $R_1$ and $R_2$ are hydrogen or straight-chain alkyl, provided that at least one of $R_1$ and $R_2$ is other than hydrogen and that $R_1$ and $R_2$ together contain no more than 9 carbon atoms, that is, the number of carbon atoms present in $R_1$ and $R_2$ together is at most 9,
and, if desired, one or more additional doping agents.

As used herein, the term "liquid crystal mixture" relates to mixtures which exhibit a nematic mesophase. Similarly, the term "nematogens" relates to materials which have a nematic mesophase.

In an electric field, liquid crystals having positive anisotropy of the dielectric constants ($\epsilon_\parallel > \epsilon_\perp$, $\epsilon_\parallel$ signifying the dielectric constant along the molecular axis and $\epsilon_\perp$ signifying the dielectric constant perpendicular thereto) orientate themselves with the direction of their largest dielectric constant, that is, with their longitudinal axes, parallel to the field direction. This effect is used, inter alia, in the interaction between embedded molecules and the liquid crystalline molecules (gues-thost interaction) described by J. H. Heilmeier and L. A. Zanoni [Applied Physics Letters 13, 91 (1968)]. Another interesting application of the dielectric field orientation exists in the rotation cell discovered by M. Schadt and W. Helfrich [Applied Physics Letters 18, (1971)] and in the Kerr cell described in Molecular Crystals and Liquid Crystals 17, 355 (1972).

The aforementioned rotation cell is essentially a condenser having transparent electrodes, the dielectric of which is formed from a nematic medium with $\epsilon_\parallel > \epsilon_\perp$. The longitudinal molecular axes of the liquid crystals are arranged in twisted form between the condenser plates in the fieldless state. The twisting structure is determined by the given wall orientation of the molecules. Upon the application of an electric potential to the condenser plates, the molecules adjust themselves with their longitudinal axes in the field direction, that is, perpendicular to the surface of the plates, by which means linear polarized light is no longer rotated in the dielectric because the liquid crystal is uniaxially perpendicular to the surface of the plates. This effect is reversible and can be used to electrically control the optical transmissivity of the condenser.

In a rotation cell of this type, it is, inter alia, desirable to use compounds or mixtures which have a low threshold and operating potential, this being important, for example, when a rotation cell display is used in clocks.

A great disadvantage of liquid crystal mixtures used today for many applications is that they exhibit too high an operation potential in rotation cell displays. This property renders impossible, for example, the direct control of wristwatch displays by a single mono cell. A further consequence of high operation potentials are the associated high residual currents which flow in the display and which result in a high power dissipation and therewith a shorter battery life. High residual currents are also disadvantageous to the life span of displays, since they accelerate electrochemical reactions which can appear on the display electrodes.

Another disadvantageous property of displays based on a field effect such as, for example, the rotation cell described earlier, is the relatively long electro-optical response time which is essentially due to the fact that the liquid crystal mixtures used today have high viscosities. Since the viscosity of a liquid rises exponentially with lowering temperature, this can cause, for example, the response times of wristwatch displays in the case of low temperatures to increase so that the indication of seconds is rendered impossible. The high viscosities of today's liquid crystal mixtures also limit the applicability to indicators of rapidly altering information, for example, in the case of matrix displays for picture information or in the case of rapid electro-optical closures.

In accordance with the present invention, it has been found that the aforementioned disadvantages of liquid crystal mixtures can be substantially reduced when the nematogenic mixture, which is to be used in the displays, is doped with one or more compounds of the formula

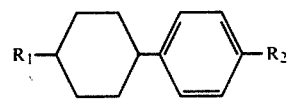

wherein $R_1$ and $R_2$ are hydrogen or straight-chain alkyl, provided that at least one of $R_1$ and $R_2$ is other than hydrogen and that the number of carbon atoms present in $R_1$ and $R_2$ together is at most 9,
and, if desired, with one or more additional doping agents.

The additional doping agent can be a compound of the formula

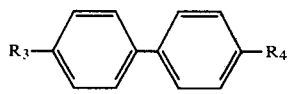

II wherein $R_3$ and $R_4$ are straight-chain alkyl containing together a sum total of at most 14 carbon atoms or $R_3$ is straight-chain alkyl and $R_4$ is straight-chain alkoxy containing together a sum total of at most 8 carbon atoms, and/or a compound of the formula

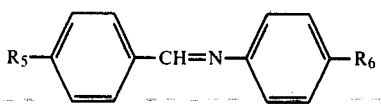

III wherein $R_5$ and $R_6$ are straight-chain alkyl containing together a sum total of at most 6 carbon atoms, and/or a compound of the formula

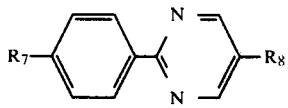

IV wherein $R_7$ and $R_8$ are the same as $R_5$ and $R_6$ as previously described herein,
and/or an organic solvent or solvent mixture having a specific resistance of at least $10^7$ ohm cm.

The number of carbon atoms present in each of $R_1$ and $R_2$ in the compounds of formula I is preferably 2–6. Preferred alkyl groups are methyl, ethyl, propyl, butyl, pentyl and hexyl.

The compounds of formula I belong to a known class of compounds and can be prepared according to known methods.

Exemplary of compounds of formula I are:
1-n-hexyl-4-cyclohexyl-benzene,
1-n-butyl-4-cyclohexyl-benzene,
1-methyl-4-(4-n-butyl-cyclohexyl)-benzene (cis and trans),
1-ethyl-4-(4-n-butyl-cyclohexyl)-benzene (cis and trans),
1-n-propyl-(4-n-propyl-cyclohexyl)-benzene (cis and trans),
1-alkyl-4-(4-n-propyl-cyclohexyl)-benzene (cis and trans) and
(4-n-butyl-cyclohexyl)-benzene (cis and trans).

At least one compound of formula I is present in the liquid crystal mixtures provided by the present invention. The number of compounds of formula I present in the liquid crystal mixtures provided by the present invention can amount, for example, to 2, 3 or 4.

The amount of compound or compounds of formula I present in the liquid crystal mixtures provided by the present invention can vary within relatively wide limits; for example, in the range of from about 1 wt.% to about 20 wt.%, preferably in the range of from about 5 wt.% to about 15 wt.%.

When the liquid crystal mixtures provided by the present invention contain an additional doping agent of formula II, III or IV or mixtures thereof, said agent is conveniently present in an amount up to about 40%, preferably in an amount in the range of from about 7% to about 30% and especially in an amount in the range of from about 10% to about 25%. When the present liquid crystal mixtures contain an organic solvent or solvent mixture and one or more compounds of formulas II, III or IV, they are conveniently present in an amount up to about 45%, preferably in an amount in the range of from about 10% to about 35% and especially in an amount in the range of from about 10% to about 25%.

The compounds of formula II are known. As mentioned earlier, when $R_3$ and $R_4$ both are straight-chain alkyl, the total number of carbon atoms is at most 14, or stated another way, no more than 14. Preferred alkyl groups are those containing 2 to 5 carbon atoms. The compounds of formula II wherein $R_3$ is alkyl containing 2 or 3 carbon atoms and $R_4$ is alkyl containing 4 or 5 carbon atoms are especially preferred. When $R_3$ is straight-chain alkyl and $R_4$ is straight-chain alkoxy, the total number of carbon atoms is at most 8, or stated another way, no more than 8. Preferred compounds in this case are those wherein each of $R_3$ and $R_4$ contain 1 to 3 carbon atoms.

The compounds of formula III are also known and the sum total of carbon atoms in $R_5$ and $R_6$ is at most 6, or stated another way, no more than 6. The compounds of formula III wherein $R_5$ and $R_6$ are each alkyl containing 1 to 4 carbon atoms are preferred. In an especially preferred compound, $R_5$ is methyl and $R_6$ is n-butyl.

As already mentioned, in the compounds of formula IV the total number of carbon atoms in $R_7$ and $R_8$ is at most 6, or stated another way, no more than 6. Preferred alkyl groups in this case are those containing 2 to 4 carbon atoms. The compound of formula IV wherein $R_7$ is ethyl and $R_8$ is n-butyl is especially preferred.

The compounds of formula IV can be prepared, for example, from p-alkylbenzamidine hydrobromide by
(a) reaction under basic conditions with an enol ether aldehyde of the formula

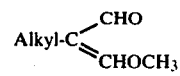

which is accessible from a 2-alkylmalonic acid tetraacetal by partial acid hydrolysis, or
(b) reacting with a 2-alkylmalonic ester to give a 2-(4'-alkylphenyl)-4-alkyl-4,6-dihydroxypyrimidine which is converted by treatment with phosphorus oxychloride into the corresponding 2-(4'-alkylphenyl)-4-alkyl-4,6-dichloropyrimidine which is then reduced with palladium/carbon and hydrogen.

The solvent or solvent mixture which may be present as the additional doping agent must, for reasons of convenience, possess a high specific resistance, namely of at least $10^7$ ohm cm, preferably of at least $10^9$ ohm cm. Furthermore, the dipole moment along the molecular axis must amount to less than 3.5 debye. In order to keep the evaporation of the solvent low at high temperatures and/or low pressures, the boiling points of the solvents or solvent mixtures as well as the heats of evaporation thereof should, moreover, be as high as possible; there are preferably used solvents and solvent mixtures whose boiling temperatures are above 100° C. at atmospheric pressure. Further, the viscosities of the solvents or solvent mixtures used should be lower than those of the nematic mixtures used when, simultaneously with the lowering of the threshold and operation potential, a viscosity-lowering of the liquid crystal mixtures is also to be achieved. It will be appreciated that the solvent or solvent mixture used must be soluble in the nematogenic mixture to be doped. Examples of solvents which fulfill the foregoing criteria are alkanes, which are straight-chain or have a —CH(CH$_3$)— group and contain a total of 8–16 carbon atoms, for example, decane, octane and 2-methylnonane; alkenes, which are straight-chain or have a —CH(CH$_3$)— group and contain a total of 8–16 carbon atoms, for example, trans dec-5-ene and trans oct-4-ene; alkynes which are straight-chain or have a —CH(CH$_3$)— group and contain a total of 8–16 carbon atoms, for example, dec-5-yne; alkyl halides, the alkyl moiety of which is straight-chain or has a —CH(CH$_3$)— group and contains a total of 6–16 carbon atoms, for example, 1-bromohexane, 1-bromododecane and 1,6-dichlorohexane; dialkyl ethers, the alkyl moieties of which are straight-chain or have a —CH(CH$_3$)— group and each contain a total of 4–8 carbon atoms, for example, dibutyl ether, dihexyl ether, dioctyl ether and propyl heptyl ether; alkyl aldehydes, the alkyl moiety of which is straight-chain or has a —CH(CH$_3$)— group and contains a total of 6–16 carbon atoms, for example, capric aldehyde and caproic aldehydes; dialkyl carbonates, the alkyl moieties of which are straight-chain or have a —CH(CH$_3$)— group and each contain a total of 2-7 carbon atoms, for example, diethyl carbonate and dibutyl carbonate; alkanecarboxylic acid alkyl esters, the alkyl moieties of which are straight-chain or have a —CH(CH$_3$)— group and together contain 6–16 carbon atoms, for example, propyl butyrate, pentyl butyrate and octyl caproate; dialkyl ketones, the alkyl moieties of which are straight-chain or have a —CH(CH$_3$)— group and each contain a total of 2–7 carbon atoms, for example, diethyl ketone, dihexyl ketone and methyl octyl ketone; monosubstituted or disubstituted, preferably paradisubstituted, benzene derivatives such as p-xylene, 1-phenylheptane, methyl p-octyl-benzoate, p-hexylhenzaldehyde or the like.

Preferred solvents are alkanes, alkyl halides, dialkyl ethers, dialkyl carbonates and alkanecarboxylic acid alkyl esters as defined earlier as well as 1-phenylheptane and p-xylene, with dialkyl ethers and alkanecarboxylic acid alkyl esters being especially preferred. Dibutyl ether, dihexyl ether, dioctyl ether, propyl butyrate and pentyl butyrate are the most preferred solvents.

The liquid crystal mixtures provided by the present invention conveniently contain in the range of from about 0.5% to about 15%, preferably in the range of from about 0.5% to about 10%, of solvent or solvent mixture. A content of solvent or solvent mixture in the range of from about 3% to about 8% is especially preferred.

The nematogenic material used consists of at least two components, so that not all compounds used as the components need themselves exhibit a nematic mesophase. In other words, the nematogenic mixture can also contain non-nematogenic substances provided that the resulting mixture is nematogenic. Similarly, not all of the compounds used as the components need have a positive anisotropy of the dielectric constants. Thus, compounds having a negative anisotropy of the dielectric constants can also be admixed and, indeed, even the mixture to be doped with solvent can exhibit a negative anisotropy of the dielectric constants; only the liquid crystal mixture provided by the present invention must have a positive anisotropy of the dielectric constants.

It is known that the addition of solvents lowers the clearing point of nematogenic mixtures, therefore such liquid crystal mixtures are only of particular interest when the nematogenic mixtures used have high clearing points before the doping. The preparation of nematogenic mixtures having high clearing points, preferably above 60° C., is well known and is accordingly not illustrated more precisely in this specification.

The nematogenic mixtures used in the present invention preferably contain compounds of the formula

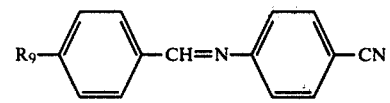

V wherein R$_9$ is straight-chain alkyl of 2 to 8 carbon atoms, straight-chain alkoxy of 4 to 7 carbon atoms, straight-chain alkanoyloxy of 2 to 8 carbon atoms or straight-chain alkylcarbonate of 2 to 11 carbon atoms, and/or compounds of the formula

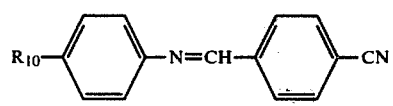

VI wherein R$_{10}$ is straight-chain alkyl of 4 to 7 carbon atoms or straight-chain alkylcarbonate of 2 to 11 carbon atoms,
and/or compounds of the formula

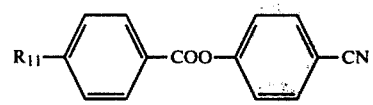

VII wherein R$_{11}$ is straight-chain alkyl of 4 to 8 carbon atoms, straight-chain alkoxy of 5 to 8 carbon atoms, straight-chain alkanoyloxy of 2 to 8 carbon atoms or straight-chain alkylcarbonate of 3 to 11 carbon atoms, and/or compounds of the formula

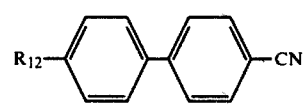

VII wherein R$_{12}$ is straight-chain alkyl of 4 to 8 carbon atoms, straight-chain alkoxy of 4 to 8 carbon atoms, straight-chain alkanoyloxy of 4 to 9 carbon atoms or straight-chain alkylcarbonate of 4 to 11 carbon atoms, and/or trans-cinnamic acid esters of the formula

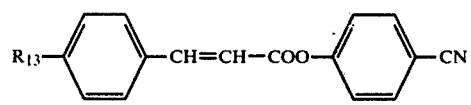

IX wherein R$_{13}$ is straight-chain alkyl of 1 to 8 carbon atoms,
and/or compounds of the formula

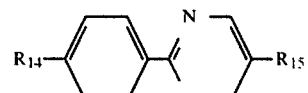

X wherein one of $R_{14}$ and $R_{15}$ is cyano and the other is straight-chain alkyl of 3 to 9 carbon atoms, straight-chain alkoxy of 2 to 9 carbon atoms or straight-chain alkanoyloxy of 2 to 9 carbon atoms, and/or compounds of the formula

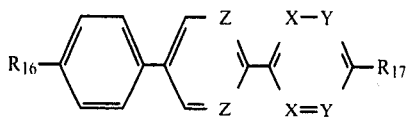

wherein one of $R_{16}$ and $R_{17}$ is hydrogen, straight-chain alkyl of 1 to 7 carbon atoms, straight-chain alkoxy of 1 to 7 carbon atoms or straight-chain alkanoyloxy of 2 to 7 carbon atoms and the other is cyano and one of X, Y and Z is nitrogen and the two others are a CH group, and/or compounds of the formula

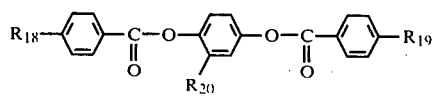

wherein $R_{18}$ and $R_{19}$ are straight-chain alkyl of 1 to 10 carbon atoms, straight-chain alkoxy of 1 to 10 carbon atoms, straight-chain alkanoyloxy of 2 to 11 carbon atoms or straight-chain alkylcarbonate of 2 to 11 carbon atoms and $R_{20}$ is chlorine, bromine or methyl, and/or compounds of the formula

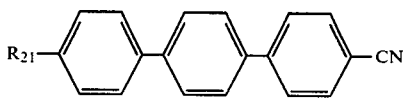

wherein $R_{21}$ is straight-chain alkyl of 3 to 8 carbon atoms.

Examples of such compounds are:
2-(4-Cyanophenyl)-5-(4-ethylphenyl)-pyrimidine,
2-(4-cyanophenyl)-5-(4-n-propylphenyl)-pyrimidine,
2-(4-cyanophenyl)-5-(4-n-butylphenyl)-pyrimidine,
2-(4-cyanophenyl)-5-(4-n-pentylphenyl)-pyrimidine,
2-(4-cyanophenyl)-5-(4-n-hexylphenyl)-pyrimidine,
2-(4-cyanophenyl)-5-(4-n-heptylphenyl)-pyrimidine,
2-(4-methylphenyl)-5-(4-cyanophenyl)-pyrimidine,
2-(4-ethylphenyl)-5-(4-cyanophenyl)-pyrimidine,
2-(4-n-propylphenyl)-5-(4-cyanophenyl)-pyrimidine,
2-(4-n-butylphenyl)-5-(4-cyanophenyl)-pyrimidine,
2-(4-n-pentylphenyl)-5-(4-cyanophenyl)-pyrimidine,
2-(4-n-hexylphenyl)-5-(4-cyanophenyl)-pyrimidine,
2-(4-n-heptylphenyl)-5-(4-cyanophenyl)-pyrimidine,
p-n-butylbenzoic acid p'-cyanophenyl ester,
p-n-pentylbenzoic acid p'-cyanophenyl ester,
p-n-hexylbenzoic acid p'-cyanophenyl ester,
p-n-heptylbenzoic acid p'-cyanophenyl ester,
p-n-octylbenzoic acid p'-cyanophenyl ester,
p-n-pentyloxybenzoic acid p'-cyanophenyl ester,
p-n-hexyloxybenzoic acid p'-cyanophenyl ester,
p-n-heptyloxybenzoic acid p'-cyanophenyl ester,
p-n-octyloxybenzoic acid p'-cyanophenyl ester,
5-n-propyl-2-(4-cyanophenyl)-pyrimidine,
5-n-butyl-2-(4-cyanophenyl)-pyrimidine,
5-n-pentyl-2-(4-cyanophenyl)-pyrimidine,
5-n-hexyl-2-(4-cyanophenyl)-pyrimidine,
5-n-heptyl-2-(4-cyanophenyl)-pyrimidine,
5-n-octyl-2-(4-cyanophenyl)-pyrimidine,
5-n-nonyl-2-(4-cyanophenyl)-pyrimidine,
4'-n-pentyl-4-cyanobiphenyl,
4-n-pentyloxy-4-cyanobiphenyl,
4-cyano-4''n-pentyl-p-terphenyl,
p-[(p-ethylbenzyliden)amino]benzonitrile,
p-[(p-n-propylbenzyliden)amino]benzonitrile,
p-[(p-n-butylbenzyliden)amino]benzonitrile,
p-[(p-n-pentylbenzyliden)amino]benzonitrile,
p-[(p-n-hexylbenzyliden)amino]benzonitrile,
p-[(p-isohexylbenzyliden)amino]benzonitrile,
p-[(p-n-heptylbenzyliden)amino]benzonitrile and
p-[(p-n-octylbenzyliden)amino]benzonitrile.

The following Examples illustrate liquid crystal mixtures provided by the present invention. These liquid crystal mixtures are based in each case on one of the following basic mixtures BM 1, BM 2 or BM 3 (in the basic mixtures all percentages are mol.%):

Basic mixture BM 1

47.3% 4'-n-pentyl-4-cyanobiphenyl,
26.7% 4'-n-pentyloxy-4-cyanobiphenyl,
6.9% 5-n-pentyl-2-(4-cyanophenyl)-pyrimidine,
11.4% 2-(4-cyanophenyl)-5-(4-n-butylphenyl)-pyrimidine and
7.7% 4-cyano-4''-n-pentyl-p-terphenyl.

Basic mixture BM 2

42.4% 4'-n-pentyl-4-cyanobiphenyl,
24.1% 4'-n-pentyloxy-4-cyanobiphenyl,
5.8% 5-n-pentyl-2-(4-cyanophenyl)-pyrimidine,
10.6% 5-n-heptyl-2-(4-cyanophenyl)-pyrimidine,
10.2% 2-(4-cyanophenyl)-5-(4-n-butylphenyl)-pyrimidine and
6.9% 4-cyano-4''-n-pentyl-p-terphenyl.

Basic mixture BM 3

10.4% p-n-butylbenzoic acid p'-cyanophenyl ester,
11.2% p-n-pentylbenzoic acid p'-cyanophenyl ester,
14.5% p-n-hexylbenzoic acid p'-n-cyanophenyl ester,
15.6% p-n-heptylbenzoic acid p'-n-cyanophenyl ester,
11.1% 5-n-pentyl-2-(4-cyanophenyl)-pyrimidine,
21.4% 5-n-heptyl-2-(4-cyanophenyl)-pyrimidine and
15.8% 2-(4-cyanophenyl)-5-(4-n-butylphenyl)-pyrimidine.

EXAMPLE 1

15 wt.% of 1-methyl-4-(4-n-butyl-cyclohexyl)-benzene are admixed with basic mixture BM 3. Clearing point 34° C.

EXAMPLE 2

15 wt.% of 1-n-butyl-4-cyclohexyl-benzene are admixed with basic mixture BM 3. Clearing point 63° C.

EXAMPLE 3

5 wt.% of 1-methyl-4-(4-n-butylcyclohexyl)-benzene are admixed with basic mixture BM 3. Clearing point 66° C.

EXAMPLE 4

8 wt.% of 1-methyl-4-(4-n-butyl-cyclohexyl)-benzene are admixed with basic mixture BM 1. Clearing point 63° C.

EXAMPLE 5

5 wt.% of 1-n-butyl-4-cyclohexyl-benzene are admixed with basic mixture BM 3. Clearing point 67° C.

EXAMPLE 6

5 wt.% of 1-n-butyl-4-cyclohexyl-benzene are admixed with basic mixture BM 1. Clearing point 73° C.

EXAMPLE 7

5 wt.% of 1-n-butyl-4-cyclohexylbenzene and 8 wt.% of 4-methyl-4'-n-pentyl-biphenyl are admixed with basic mixture BM 3. Clearing point 60° C.

EXAMPLE 8

5 wt.% of 1-n-hexyl-4-cyclohexyl-benzene are admixed with basic mixture BM 1. Clearing point 74° C.

EXAMPLE 9

5 wt.% of 1-n-hexyl-4-cyclohexyl-benzene and 7 wt.% of 4-methyl-4'-n-pentyl-biphenyl are admixed with basic mixture BM 3. Clearing point 61° C.

EXAMPLE 10

5 wt.% of 1-n-hexyl-4-cyclohexylbenzene are admixed with basic mixture BM 2. Clearing point 70° C.

EXAMPLE 11

8 wt.% of 1-n-hexyl-4-cyclohexyl-benzene are admixed with basic mixture BM 1. Clearing point 65° C.

EXAMPLE 12

5 wt.% of cis-1-methyl-4-(4-n-propyl-cyclohexyl)-benzene are admixed with basic mixture BM 3. Clearing point 66° C.

EXAMPLE 13

5 wt.% of trans-1-methyl-4-(4-n-propyl-cyclohexyl)-benzene are admixed with basic mixture BM 3. Clearing point 74° C.

EXAMPLE 14

5 wt.% of cis-1-n-propyl-4-(4-n-propyl-cyclohexyl)-benzene are admixed with basic mixture BM 3. Clearing point 67° C.

EXAMPLE 15

5 wt.% of trans-1-n-propyl-4-(4-n-propyl-cyclohexyl)-benzene are admixed with basic mixture BM 3. Clearing point 75° C.

EXAMPLE 16

3 wt.% of 1-n-hexyl-4-cyclohexyl-benzene and 4% of dihexyl ether are admixed with basic mixture BM 3. Clearing point 60°-65° C.

EXAMPLE 17

6 wt.% of 4-methyl-4'-n-pentyl-biphenyl and 8 wt.% of 1-n-hexyl-4-cyclohexyl-benzene are admixed with basic mixture BM 3. Clearing point 57°-59° C.

EXAMPLE 18

4 wt.% of 4-methyl-4'-n-pentyl-biphenyl and 9 wt.% of 1-n-hexyl-4-cyclohexyl-benzene are admixed with basic mixture BM 3. Clearing point 54°-58° C.

The percentages for the mixed compounds given in the foregoing Example 1-18 relate in each case to the total weight of the finished liquid crystal mixture.

When used in a rotation cell, the liquid crystal mixtures obtained according to the foregoing Examples 1-18 are characterised by lower threshold and operation potential, lower reclaim times, high ohmicity and no or insignificant variation of the total composition (on the basis of the high boiling point of the additive of formula I).

The preparation of compounds of formula I which are especially suitable for use in the liquid crystal mixtures provided by the present invention is described in Examples A-H hereinafter:

Example A

A mixture of 53.5 g of 1-(p-cyclohexylphenyl)-1-hexanone, 160 ml of ethanol, 198 ml of diethyleneglycol and 19.7 ml of hydrazine hydrate is left to stand at room temperature overnight, treated while stirring with 25.5 g of potassium hydroxide, heated to 200°-210° C. while simultaneously distilling-off the volatile constituents over a period of 2 hours and left at 200°-210° C. for 1.5 hours. After cooling, the mixture is diluted with 300 ml of water and exhaustively extracted with ether. The organic layer is washed neutral with water, dried over sodium sulfate and freed from solvent in vacuo. For purification, the resulting 49.6 g of crude 1-n-hexyl-4-cyclohexyl-benzene are distilled in a rotary bulb-tube at 0.003 mm/100° C., there being obtained 42.2 g of colorless oil having a purity of greater than 99% according to gas chromatography.

The 1-(p-cyclohexylphenyl)-1-hexanone used as the starting material can be prepared as follows:

A mixture of 40.1 g of cyclohexylbenzene, 40.4 g of caproyl chloride and 310 ml of methylene chloride is treated portionwise while stirring over a period of 10 minutes with 40.0 g of anhydrous aluminum chloride, stirred at room temperature for 2 hours, boiled under reflux for 2 hours and, after cooling, poured into a mixture of 125 ml of concentrated hydrochloric acid and 500 ml of ice/water. The mixture is exhaustively extracted with methylene chloride, the organic phase is washed with 3-N sodium hydroxide and, after drying over sodium sulfate, the solvent is removed in vacuo. For purification, the resulting 65.0 g of crude 1-(p-cyclohexylphenyl)-1-hexanone are distilled in a rotary bulb-tube at 0.1 mm/145°-155° C., there being obtained 53.7 g of colorless crystals of melting point 40.0°-40.9° C.

Example B

A solution of 35.5 g of 1-(p-cyclohexylphenyl)-1-butanone in 350 ml of rectified alcohol is hydrogenated at 50°-55° C. with 4.0 g of palladium/carbon catalyst (10% palladium) until 2 mol of hydrogen are taken up and the hydrogenation has come to a standstill. After cooling, the catalyst is separated by filtration and the solvent is removed in vacuo. The resulting 33.6 g of crude 1-n-butyl-4-cyclohexyl-benzene are dissolved in 200 ml of n-hexane and filtered through a column of 300 g of silica gel in n-hexane. Elution with hexane yields 31.8 g of colorless oil which, for further purification, is distilled in a rotary bulb-tube at 0.01 mm/90°-100° C.; there being obtained 30.3 g of product having a purity of greater than 99% according to gas chromatography.

The 1-(p-cyclohexylphenyl)-1-butanone used as the starting material can be prepared as described in Example A by reacting cyclohexylbenzene with butyryl chloride and aluminum chloride in methylene chloride, there being obtained colorless crystals of melting point 41.2°-42.1° C.

Example C 2.340 g of trans-1-methyl-4-(1-hydroxy-4-n-butylcyclohexyl)-benzene in 40 ml of rectified alcohol are hydrogenated at room temperature with 0.3 g of palladium/carbon catalyst (5% palladium) until the hydrogenation comes to a standstill after the uptake of 1 mol of hydrogen. The catalyst is removed by filtration and the solvent is removed in vacuo. The crude cis-1-methyl-4-(4-n-butyl-cyclohexyl)-benzene is dissolved in n-hexane and filtered through a column of 90 g of silica gel in n-hexane. Elution with hexane yields 2.132 g of colorless oil which, for further purification, is distilled in a rotary bulb-tube at 0.05 mm/100°-120° C., there being obtained 2.006 g of product having a purity of greater than 97% according to gas chromatography.

3.517 g of cis-1-methyl-4-(1-hydroxy-4-n-butyl-cyclohexyl)-benzene in 60 ml of rectified alcohol are hydrogenated as described in the preceding paragraph with 0.5 g of palladium/carbon catalyst. Similar work-up and purification yield, after distillation at 0.05 mm/100°-120° C., 2.808 g of trans-1-methyl-4-(4-n-butyl-cyclohexyl)-benzene having a purity of greater than 97% according to gas chromatography.

The trans- and cis-1-methyl-4-(1-hydroxy-4-n-butyl-cyclohexyl)-benzenes used as the starting materials are prepared in the ratio 23:35 by a Grignard reaction of p-methyl-phenylmagnesium bromide (obtained from 0.802 g of magnesium shavings and 5.640 g of 4-bromotoluene in ether) with 4.620 g of 4-n-butyl-cyclohexanone in ether according to the procedure described in J. Amer. Chem. Soc. 85, 3228 (1963) and are separated by chromatography on silica gel as described therein.

Example D

In a manner analogous to that described in Example C, 1.496 g of trans-1-ethyl-4-(1-hydroxy-4-n-butyl-cyclohexyl)-benzene in 30 ml of rectified alcohol are hydrogenated at room temperature with 0.25 g of palladium/carbon catalyst, the mixture is worked-up and the crude cis-1-ethyl-4-(4-n-butyl-cyclohexyl)-benzene is purified. After distillation at 0.05 mm/140°-150° C., there are obtained 1.21 g of colorless oil having a purity of greater than 97% according to gas chromatography.

In a manner analogous to that described in Example C, 3.293 g of cis-1-ethyl-4-(1-hydroxy-4-n-butyl-cyclohexyl)-benzene in 60 ml of rectified alcohol are hydrogenated at room temperature with 0.45 g of palladium/carbon catalyst, the mixture is worked-up and the crude trans-1-ethyl-4-(4-n-butyl-cyclohexyl)-benzene is purified. After distillation at 0.05 mm/140°-150° C., there are obtained 2.856 g of colorless oil having a purity of greater than 97% according to gas chromatography.

The trans- and cis-1-ethyl-4-(1-hydroxy-4-n-butyl-cyclohexyl)-benzenes used as the starting materials are prepared in the ratio 3:4 by a Grignard reaction of p-ethyl-phenylmagnesium bromide (obtained from 0.802 g of magnesium shavings and 6.718 g of p-ethyl-bromobenzene in ether) with 4.620 g of 4-n-butyl-cyclohexanone in ether according to the details given in Example C.

Example E 1.344 g of trans-1-ethyl-4-(1-hydroxy-4-n-butyl-cyclohexyl)-benzene in 30 ml of rectified alcohol are hydrogenated at room temperature with 6.0 g of ethanol-moist Raney-nickel at room temperature until the hydrogenation comes to a standstill after the uptake of 1 mol of hydrogen. The working-up is carried out as described in Example C and there are obtained, after distillation at 0.05 mm/140°-150° C., 1.087 g of colorless oily trans-1-ethyl-4-(4-n-butyl-cyclohexyl)-benzene having a purity of greater than 97% according to gas chromatography.

1.563 g of cis-1-ethyl-4-(1-hydroxy-4-n-butyl-cyclohexyl)-benzene in 40 ml of rectified alcohol are hydrogenated in the manner described in the preceding paragraph with 7.5 g of ethanol-moist Raney-nickel, worked-up and the crude cis-1-ethyl-4-(4-n-butyl-cyclohexyl)-benzene is purified as described in Example C. After distillation at 0.05 mm/140°-150° C., there are obtained 1.286 g of colorless oil having a purity of greater than 97% according to gas chromatography.

Example F

In a manner analogous to that described in Example C, 2.810 g of trans-1-n-propyl-4-(1-hydroxy-4-n-propyl-cyclohexyl)-benzene in 50 ml of rectified alcohol are hydrogenated at room temperature with 0.60 g of palladium/carbon catalyst, the mixture is worked-up and the crude cis-1-n-propyl-4-(4-n-propyl-cyclohexyl)-benzene is purified. After distillation at 0.035 mm/115°-125° C., there are obtained 2.263 g of colorless oil having a purity of greater than 97% according to gas chromatography.

In a manner analogous to that described in Example C, 2.913 g of cis-1-n-propyl-4-(1-hydroxy-4-n-propyl-cyclohexyl)-benzene in 50 ml of rectified alcohol are hydrogenated at room temperature with 0.62 g of palladium/carbon catalyst, the mixture is worked-up and the crude trans-1-n-propyl-4-(4-n-propyl-cyclohexyl)-benzene is purified. After distillation at 0.035 mm/120°-130° C., there are obtained 2.135 g of colorless oil having a purity of greater than 97% according to gas chromatography.

The trans- and cis-1-n-propyl-4-(1-hydroxy-4-n-propyl-cyclohexyl)-benzenes used as the starting materials are prepared in the ratio 28:29 by a Grignard reaction of p-n-propyl-phenylmagnesium bromide (obtained from 0.802 g of magnesium shavings and 7.227 g of p-n-propyl-bromobenzene in ether) with 4.206 g of 4-n-propyl-cyclohexane in ether according to the details given in Example C.

Example G

In a manner analogous to that described in Example C, 2.292 g of trans-1-ethyl-4-(1-hydroxy-4-n-propyl-cyclohexyl)-benzene in 45 ml of rectified alcohol are hydrogenated at room temperature with 0.52 g of palladium/carbon catalyst, the product is worked-up and the crude cis-1-ethyl-4-(4-n-propyl-cyclohexyl)-benzene is purified. After distillation at 0.08 mm/120°-135° C., there are obtained 1.849 g of colorless oil having a purity of greater than 97% according to gas chromatography.

In a manner analogous to that described in Example C, 3.252 g of cis-1-ethyl-4-(1-hydroxy-4-n-propyl-cyclohexyl)-benzene in 60 ml of rectified alcohol are hydrogenated at room temperature with 0.73 g of palladium/carbon catalyst, the mixture is worked-up and the crude trans-1-ethyl-4-(4-n-propyl-cyclohexyl)-benzene is purified. After distillation at 0.02 mm/120° C., there are obtained 1.633 g of colorless oil having a purity of greater than 97% according to gas chromatography.

The trans- and cis-1-ethyl-4-(1-hydroxy-4-n-propyl-cyclohexyl)-benzenes used as the starting materials are prepared in the ratio 11:16 by a Grignard reaction of p-ethyl-phenylmagnesium bromide (obtained from 0.802 g of magnesium shavings and 6.718 g of p-ethyl-bromobenzene in ether) with 4.206 g of 4-n-propyl-cyclohexanone in ether according to the details given in Example C.

Example H

In a manner analogous to that described in Example C, 3.069 g of trans-(1-hydroxy-4-n-butyl-cyclohexyl)-benzene in 60 ml of rectified alcohol are hydrogenated at room temperature with 0.73 g of palladium/carbon catalyst, the mixture is worked-up and the crude cis-(4-n-butyl-cyclohexyl)-benzene is purified. After distillation at 0.02 mm/85°–95° C., there are obtained 2.351 g of colorless oil having a purity of greater than 97% according to gas chromatography.

In a manner analogous to that described in Example C, 3.203 g of cis-(1-hydroxy-4-n-butyl-cyclohexyl)-benzene in 60 ml of rectified alcohol are hydrogenated at room temperature with 0.75 g of palladium/carbon catalyst, the mixture is worked-up and the crude trans-(4-n-butyl-cyclohexyl)-benzene is purified. After distillation at 0.02 mm/85°–95° C., there are obtained 1.608 g of colorless oil having a purity of 97% according to gas chromatography.

The trans- and cis-(1-hydroxy-4-n-butyl-cyclohexyl)-benzenes used as the starting materials are prepared in the ratio 15:16 by a Grignard reaction of phenylmagnesium bromide (obtained from 0.802 g of magnesium shavings and 5.699 g of bromobenzene in ether) with 4.628 g of 4-n-butyl-cyclohexanone in ether according to the details given in Example C.

We claim:

1. A nematic liquid crystal mixture having positive anisotropy of the dielectric constants comprising a nematogenic material having a clearing point above 60° C. and one or more compounds of the formula

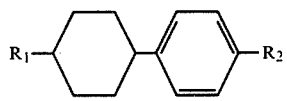

wherein $R_1$ and $R_2$ are hydrogen or straight-chain alkyl, provided that at least one of $R_1$ and $R_2$ is other than hydrogen and that the sum of the number of carbon atoms present in $R_1$ and $R_2$ is at most 9.

2. A nematic liquid crystal mixture in accordance with claim 1, further comprising as an additional doping agent a compound of the formula

wherein $R_3$ and $R_4$ are straight-chain alkyl containing a total of at most 14 carbon atoms or $R_3$ is straight-chain alkyl and $R_4$ is straight-chain alkoxy containing together a total of at most 8 carbon atoms,
and/or a compound of the formula

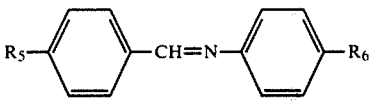

wherein $R_5$ and $R_6$ are straight-chain alkyl containing together a total of at most 6 carbon atoms,
and/or a compound of the formula

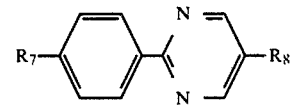

wherein $R_7$ and $R_8$ are the same as $R_5$ and $R_6$ described above,
and/or any other organic solvent or solvent mixture having a specific resistance of at least $10^7$ ohm cm.

3. A nematic liquid crystal mixture in accordance with claim 2, wherein the compound of formula I is present in an amount in the range of from about 1 wt.% to about 20 wt.%.

4. A nematic liquid crystal mixture in accordance with claim 3, wherein the compound of formula I is present in an amount in the range of from about 5 wt.% to about 15 wt.%.

5. A nematic liquid crystal mixture in accordance with claim 4, wherein the number of carbon atoms present in each of $R_1$ and $R_2$ in the compound of formula I is 2–6.

6. A nematic liquid crystal mixture in accordance with claim 5, wherein the compound of formula I is 1-n-hexyl-4-cyclohexyl-benzene, 1-n-butyl-4-cyclohexyl-benzene, 1-methyl-4-(4-n-butyl-cyclohexyl)-benzene, 1-ethyl-4-(4-n-butyl-cyclohexyl)-benzene, 1-n-propyl-(4-n-propyl-cyclohexyl)-benzene, 1-ethyl-4-(4-n-propyl-cyclohexyl)-benzene or (4-n-butyl-cyclohexyl)-benzene.

7. A nematic liquid crystal mixture in accordance with any one of claims 1, 2, 3, 4, 5 or 6, wherein the nematogenic material comprises one or more compounds of the formula

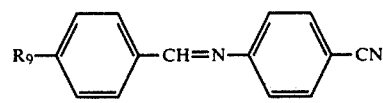

wherein $R_9$ is straight-chain alkyl of 2 to 8 carbon atoms, straight-chain alkoxy of 4 to 7 carbon atoms, straight-chain alkanoyloxy of 2 to 8 carbon atoms or straight-chain alkylcarbonate of 2 to 11 carbon atoms,
and/or one or more compounds of the formula

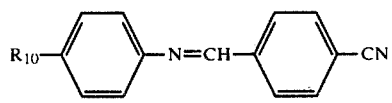

wherein $R_{10}$ is straight-chain alkyl of 4 to 7 carbon atoms or straight-chain alkylcarbonate of 2 to 11 carbon atoms,
and/or one or more compounds of the formula

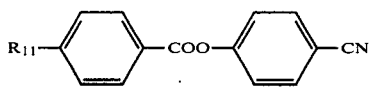

wherein R₁₁ is straight-chain alkyl of 4 to 8 carbon atoms, straight-chain alkoxy of 5 to 8 carbon atoms, straight-chain alkanoyloxy of 2 to 8 carbon atoms or straight-chain alkylcarbonate of 3 to 11 carbon atoms, and/or one or more compounds of the formula

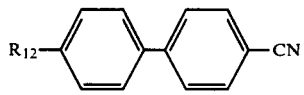

wherein R₁₂ is straight-chain alkyl of 4 to 8 carbon atoms, straight-chain alkoxy of 4 to 8 carbon atoms, straight-chain alkanoyloxy of 4 to 9 carbon atoms or straight-chain alkylcarbonate of 4 to 11 carbon atoms, and/or one or more trans-cinnamic acid esters of the formula

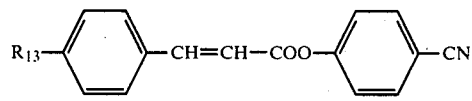

wherein R₁₃ is straight-chain alkyl of 1 to 8 carbon atoms,
and/or one or more compounds of the formula

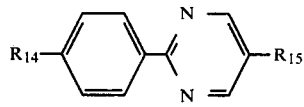

wherein one of R₁₄ and R₁₅ are cyano and the other is straight-chain alkyl of 3 to 9 carbon atoms, straight-chain alkoxy of 2 to 9 carbon atoms or straight-chain alkanoyloxy of 2 to 9 carbon atoms,
and/or one or more compounds of the formula

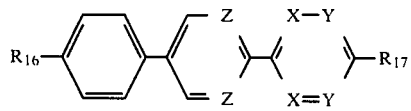

wherein one of R₁₆ and R₁₇ is hydrogen, straight-chain alkyl of 1 to 7 carbon atoms, straight-chain alkoxy of 1 to 7 carbon atoms or straight-chain alkanoyloxy of 2 to 7 carbon atoms and the other is cyano and one of X, Y and Z is nitrogen and the two others are a CH group,
and/or one or more compounds of the formula

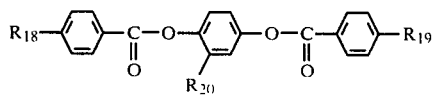

wherein R₁₈ and R₁₉ are straight-chain alkyl of 1 to 10 carbon atoms, straight-chain alkoxy of 1 to 10 carbon atoms, straight-chain alkanoyloxy of 2 to 11 carbon atoms or straight-chain alkylcarbonate of 2 to 11 carbon atoms and R₂₀ is chlorine, bromine or methyl,
and/or one or more compounds of the formula

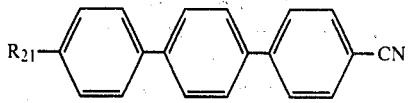

wherein R₂₁ is straight-chain alkyl of 3 to 8 carbon atoms.

8. A nematic liquid crystal mixture in accordance with claim 1 which contains p-n-butylbenzoic acid p'-cyanophenyl ester, p-n-pentylbenzoic acid p'-cyanophenyl ester, p-n-hexylbenzoic acid p'-cyanophenyl ester, p-n-heptylbenzoic acid p'-cyanophenyl ester, 5-n-pentyl-2-(4-cyanophenyl)-pyrimidine, 5-n-heptyl-2-(4-cyanophenyl)-pyrimidine, 2-(4-cyanophenyl)-5-(4-n-butylphenyl)-pyrimidine, 1-n-hexyl-4-cyclohexyl-benzene and 4-methyl-4'-n-pentyl-biphenyl.

9. A nematic liquid crystal mixture in accordance with claim 8 which contains 8.7 wt.% p-n-butylbenzoic acid p'-cyanophenyl ester, 9.84 wt.% p-n-pentylbenzoic acid p'-cyanophenyl ester, 13.35 wt.% p-n-hexylbenzoic acid p'-cyanophenyl ester, 15.02 wt.% p-n-heptylbenzoic acid p'-cyanophenyl ester, 8.35 wt.% 5-n-pentyl-2-(4-cyanophenyl)-pyrimidine, 17.91 wt.% 5-n-heptyl-2-(4-cyanophenyl)-pyrimidine, 15.8 wt.% 2-(4-cyanophenyl)-5-(4-n-butylphenyl)-pyrimidine, 5 wt.% 1-n-hexyl-4-cyclohexyl-benzene and 7 wt.% 4-methyl-4'-n-pentyl-biphenyl.

10. A nematic liquid crystal mixture in accordance with claim 1 which contains 4'-n-pentyl-4-cyanobiphenyl, 4'-n-pentyloxy-4-cyanobiphenyl, 5-n-pentyl-2-(4-cyanophenyl)-pyrimidine, 5-n-heptyl-2-(4-cyanophenyl)-pyrimidine, 2-(4-cyanophenyl)-5-(4-n-butylphenyl)-pyrimidine, 4-cyano-4''-n-pentyl-p-terphenyl and 1-n-hexyl-4-cyclohexyl-benzene.

11. A nematic liquid crystal mixture in accordance with claim 10 which contains 37.44 wt.% 4'-n-pentyl-4-cyanobiphenyl, 22.65 wt.% 4'-n-pentyloxy-4-cyanobiphenyl, 5.16 wt.% 5-n-pentyl-2-(4-cyanophenyl)-pyrimidine, 10.49 wt.% 5-n-heptyl-2-(4-cyanophenyl)-pyrimidine, 11.31 wt.% 2-(4-cyanophenyl)-5-(4-n-butylphenyl)-pyrimidine, 7.95 wt.% 4-cyano-4''-n-pentyl-p-terphenyl and 5 wt.% 1-n-hexyl-4-cyclohexyl-benzene.

12. A nematic liquid crystal mixture in accordance with claim 8 which contains 8.7 wt.% p-n-butylbenzoic acid p'-cyanophenyl ester, 9.84 wt.% p-n-pentylbenzoic acid p'-cyanophenyl ester, 13.35 wt.% p-n-hexylbenzoic acid p'-cyanophenyl ester, 15.02 wt.% p-n-heptylbenzoic acid p'-cyanophenyl ester, 8.35 wt.% 5-n-pentyl-2-(4-cyanophenyl)-pyrimidine, 17.91 wt.% 5-n-heptyl-2-(4-cyanophenyl)-pyrimidine, 15.8 wt.% 2-(4-cyanophenyl)-5-(4-n-butylphenyl)-pyrimidine, 8 wt.% 1-n-hexyl-4-cyclohexyl-benzene and 6 wt.% 4-methyl-4'-n-pentyl-biphenyl.

13. A nematic liquid crystal mixture in accordance with claim 8 which contains 8.7 wt.% p-n-butylbenzoic acid p'-cyanophenyl ester, 9.84 wt.% p-n-pentylbenzoic acid p'-cyanophenyl ester, 13.35 wt.% p-n-hexylbenzoic acid p'-cyanophenyl ester, 15.02 wt.% p-n-heptylbenzoic acid p'-cyanophenyl ester, 8.35 wt.% 5-n-pentyl-2-(4-cyanophenyl)-pyrimidine, 17.91 wt.% 5-n-heptyl-2-(4-cyanophenyl)-pyrimidine, 15.8 wt.% 2-(4-cyanophenyl)-5-(4-n-butylphenyl)-pyrimidine, 9 wt.% rity of greater than 97% according to gas chromatography.

The trans- and cis-1-ethyl-4-(1-hydroxy-4-n-propylcyclohexyl)-benzenes used as the starting materials are prepared in the ratio 11:16 by a Grignard reaction of p-ethyl-phenylmagnesium bromide (obtained from 0.802 g of magnesium shavings and 6.718 g of p-ethyl-bromobenzene in ether) with 4.206 g of 4-n-propyl-cyclohexanone in ether according to the details given in Example C.

Example H

In a manner analogous to that described in Example C, 3.069 g of trans-(1-hydroxy-4-n-butyl-cyclohexyl)-benzene in 60 ml of rectified alcohol are hydrogenated at room temperature with 0.73 g of palladium/carbon catalyst, the mixture is worked-up and the crude cis-(4-n-butyl-cyclohexyl)-benzene is purified. After distillation at 0.02 mm/85°–95° C., there are obtained 2.351 g of colorless oil having a purity of greater than 97% according to gas chromatography.

In a manner analogous to that described in Example C, 3.203 g of cis-(1-hydroxy-4-n-butyl-cyclohexyl)-benzene in 60 ml of rectified alcohol are hydrogenated at room temperature with 0.75 g of palladium/carbon catalyst, the mixture is worked-up and the crude trans-(4-n-butyl-cyclohexyl)-benzene is purified. After distillation at 0.02 mm/85°–95° C., there are obtained 1.608 g of colorless oil having a purity of 97% according to gas chromatography.

The trans- and cis-(1-hydroxy-4-n-butyl-cyclohexyl)-benzenes used as the starting materials are prepared in the ratio 15:16 by a Grignard reaction of phenylmagnesium bromide (obtained from 0.802 g of magnesium shavings and 5.699 g of bromobenzene in ether) with 4.628 g of 4-n-butyl-cyclohexanone in ether according to the details given in Example C.

We claim:

1. A nematic liquid crystal mixture having positive anisotropy of the dielectric constants comprising a nematogenic material having a clearing point above 60° C. and one or more compounds of the formula

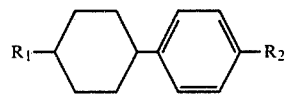

I wherein $R_1$ and $R_2$ are hydrogen or straight-chain alkyl, provided that at least one of $R_1$ and $R_2$ is other than hydrogen and that the sum of the number of carbon atoms present in $R_1$ and $R_2$ is at most 9.

2. A nematic liquid crystal mixture in accordance with claim 1, further comprising as an additional doping agent a compound of the formula

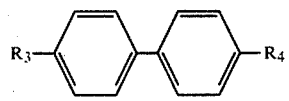

II wherein $R_3$ and $R_4$ are straight-chain alkyl containing a total of at most 14 carbon atoms or $R_3$ is straight-chain alkyl and $R_4$ is straight-chain alkoxy containing together a total of at most 8 carbon atoms, and/or a compound of the formula

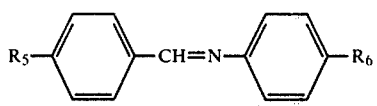

III wherein $R_5$ and $R_6$ are straight-chain alkyl containing together a total of at most 6 carbon atoms, and/or a compound of the formula

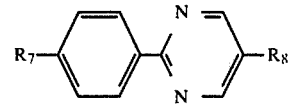

IV wherein $R_7$ and $R_8$ are the same as $R_5$ and $R_6$ described above, and/or any other organic solvent or solvent mixture having a specific resistance of at least $10^7$ ohm cm.

3. A nematic liquid crystal mixture in accordance with claim 2, wherein the compound of formula I is present in an amount in the range of from about 1 wt.% to about 20 wt.%.

4. A nematic liquid crystal mixture in accordance with claim 3, wherein the compound of formula I is present in an amount in the range of from about 5 wt.% to about 15 wt.%.

5. A nematic liquid crystal mixture in accordance with claim 4, wherein the number of carbon atoms present in each of $R_1$ and $R_2$ in the compound of formula I is 2–6.

6. A nematic liquid crystal mixture in accordance with claim 5, wherein the compound of formula I is 1-n-hexyl-4-cyclohexyl-benzene, 1-n-butyl-4-cyclohexyl-benzene, 1-methyl-4-(4-n-butyl-cyclohexyl)-benzene, 1-ethyl-4-(4-n-butyl-cyclohexyl)-benzene, 1-n-propyl-(4-n-propyl-cyclohexyl)-benzene, 1-ethyl-4-(4-n-propyl-cyclohexyl)-benzene or (4-n-butyl-cyclohexyl)-benzene.

7. A nematic liquid crystal mixture in accordance with any one of claims 1, 2, 3, 4, 5 or 6, wherein the nematogenic material comprises one or more compounds of the formula

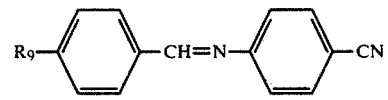

V wherein $R_9$ is straight-chain alkyl of 2 to 8 carbon atoms, straight-chain alkoxy of 4 to 7 carbon atoms, straight-chain alkanoyloxy of 2 to 8 carbon atoms or straight-chain alkylcarbonate of 2 to 11 carbon atoms, and/or one or more compounds of the formula

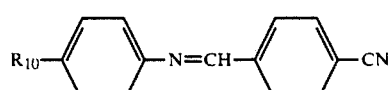

VI wherein $R_{10}$ is straight-chain alkyl of 4 to 7 carbon atoms or straight-chain alkylcarbonate of 2 to 11 carbon atoms, and/or one or more compounds of the formula